United States Patent
Leijssen et al.

(10) Patent No.: US 8,390,416 B2
(45) Date of Patent: Mar. 5, 2013

(54) REUSE OF SCREW THREAD

(75) Inventors: Jacobus Josephus Leijssen, Eindhoven (NL); Jeroen Jacob Arnold Tol, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/125,091

(22) PCT Filed: Oct. 21, 2009

(86) PCT No.: PCT/IB2009/054635
§ 371 (c)(1),
(2), (4) Date: Apr. 20, 2011

(87) PCT Pub. No.: WO2010/049849
PCT Pub. Date: May 6, 2010

(65) Prior Publication Data
US 2011/0199173 A1    Aug. 18, 2011

(30) Foreign Application Priority Data
Oct. 28, 2008  (EP) .................................... 08167695

(51) Int. Cl.
*H01F 27/28* (2006.01)
*H01F 27/02* (2006.01)
*A61N 1/00* (2006.01)
(52) U.S. Cl. .............................. 336/195; 336/92; 607/65
(58) Field of Classification Search .................. 336/185, 336/195, 92; 607/60, 61, 65
See application file for complete search history.

(56) References Cited

U.S. PATENT DOCUMENTS

| | | | | |
|---|---|---|---|---|
| 1,837,413 A * | 12/1931 | Dobson | .......................... | 336/195 |
| 1,896,948 A * | 2/1933 | Gough | .......................... | 439/690 |
| 6,268,785 B1 | 7/2001 | Kollman | | |
| 6,499,488 B1 * | 12/2002 | Hunter et al. | ................. | 128/899 |
| 6,631,296 B1 | 10/2003 | Parramon | | |

(Continued)

FOREIGN PATENT DOCUMENTS

| | | |
|---|---|---|
| EP | 0889541 A1 | 1/1999 |
| EP | 1271573 A2 | 1/2003 |
| GB | 2317271 A | 3/1998 |
| WO | 9926316 A1 | 5/1999 |

OTHER PUBLICATIONS

Glossop, Neil et al "Magnetically Tracked Bone Screws; A New Tool for Minimally Invasive CAOS", International Society for Computer Assisted Orthopaedic Surger, Jun. 2003.

*Primary Examiner* — Mohamad Musleh
*Assistant Examiner* — Joselito Baisa

(57) ABSTRACT

Components having a screw thread useful for mechanical fixation of the component to a corresponding component may be equipped with electrical wire following at least part of the turns of the screw thread and thereby forming at least a part of a coil. The corresponding component may have a matching screw thread, or the component of the invention may be self-tapping, in which case a matching screw thread in the corresponding component would be superfluous. The coil may be used as charging and/or power-conversion coil and/or communication antenna. The reuse of the screw thread for a coil maximizes the coil area without consuming extra space of the component. This is in particular useful in medical electrical implant devices, such as a pace maker or a neuron pace maker in deep brain stimulation, in that the maximum size of such a pace maker is very limited. Moreover, the screw thread of such components may additionally comprise connectors for providing electrical connection to other electrical parts in a matching component.

12 Claims, 8 Drawing Sheets

U.S. PATENT DOCUMENTS

| | | | |
|---|---|---|---|
| 6,877,997 B2 * | 4/2005 | Schaty | 439/92 |
| 7,275,448 B2 * | 10/2007 | Bitto et al. | 73/861.355 |
| 8,046,050 B2 * | 10/2011 | Govari et al. | 600/424 |
| 8,125,469 B2 * | 2/2012 | Badaye et al. | 345/179 |
| 2005/0238461 A1 * | 10/2005 | Lutkus et al. | 411/438 |
| 2007/0141887 A1 | 6/2007 | Kuo | |
| 2007/0250981 A1 | 11/2007 | Seibert | |
| 2010/0221087 A1 * | 9/2010 | Gillis | 411/438 |
| 2011/0097178 A1 * | 4/2011 | Stiebitz et al. | 411/387.4 |

* cited by examiner

REUSE OF SCREW THREAD

FIELD OF THE INVENTION

The present invention relates to a component comprising an electrical wire. The present invention moreover relates to modular systems comprising two components, whereof at least one of the components comprises an electrical wire.

BACKGROUND OF THE INVENTION

Power and data interfaces are widely used in many devices and components to transfer data and power from an external source. Such power and data interfaces may be wireless or wired. A coil of electrical wire may be used wired or wirelessly for transferring information, e.g. receiving an RF signal, and/or energy, e.g. a voltage converter.

The document U.S. Pat. No. 6,631,296 discloses a voltage converter for use within small implantable electrical devices, where the voltage converter comprises a coil to provide voltage conversion. The coil may be used in a time-multiplexing scheme to provide for both the receipt of RF signals and a voltage conversion function.

Even though U.S. Pat. No. 6,631,296 describes the advantageous use of a coil as both RF antenna and voltage converter, in order to free up space within an implantable device, it would be advantageous to minimize the space taken up by the coil.

Hence, an improved component comprising an electrical wire would be advantageous, and in particular a more compact component would be advantageous.

SUMMARY OF THE INVENTION

Accordingly, it may be seen as an object of the present invention to provide a compact component comprising an electrical wire.

This object and several other objects are obtained in a first aspect of the invention by providing a component having a screw thread for fastening, wherein an electrical wire is arranged at least partly within the thread of said screw thread and wherein the electrical wire follows at least part of the turns of the screw thread.

The invention is particularly, but not exclusively, advantageous for obtaining a component having an electrical wire forming a coil, wherein a screw thread of the component is reused for the turns of the coil. Hereby, a compact component may be achieved since the electrical wire is not taking up useful space within the bulk of the component. The term "follows part of the turns" is meant to include examples where only part of a single turn is followed and examples where some turns or all of the turns of the screw thread are followed.

The coil windings may be embedded or integrated within the material of the thread of the screw thread. Alternatively, an electrical wire may constitute the thread or part thereof. Such an electrical wire constituting the thread or part of the thread of a component would typically be insulated; however, if all other materials are non-conducting and if a coil of only a single turn is needed, a non-insulated wire could also be used.

The screw thread of the component may be an external (male) thread—or an internal (female) thread. The coil may be applied for any appropriate use, such as for charging, power conversion, communication, etc. The component is particularly advantageous for uses where the component size is of high importance, such as for instance in medical implantable devices.

The reuse of the screw thread of a component results in the maximum possible coil surface as the coil is close to the outer surface of the component. Therefore the best efficiency and coupling factor to an external inductive RF field is achieved without an extra space penalty as if a stand-alone coil would be included in the component itself.

In an embodiment of the invention, at least part of the turns of the screw thread comprises more than one coil winding of electrical wire. This is advantageous in a situation where the number of turns of the screw thread is lower than the number of turns required for the coil integrated in the screw thread.

According to an aspect of the component, the electrical wire comprises a return part.

An electrical wire may be wound more than once within the same screw thread and at the end of the screw thread, the wire can be brought to the starting point of the screw thread for extra turns. The relatively small return part of the wire, substantially perpendicular to the turns of the coil, may be integrated in the housing. The magnetic field of the return part(s) is orthogonal to the magnetic field from the turns of the electrical wire within the screw thread, and therefore, ideally, they do not influence each other. The number of windings embedded or integrated within the screw thread is limited by the applied wire thickness and the mechanical specifications of the screw thread.

According to another embodiment, the coil is arranged to perform more than one electromagnetic function, wherein frequency filters separate the more than one electromagnetic function. The more than one electromagnetic function may comprise one or more of the following: receiving or transmitting as an RF antenna, receiving energy, for example for charging a battery, voltage conversion. The various electromagnetic functions may be split e.g. by frequency filters. Thus, the same coil may be used for a range of different functions. The coil may be split into various parts for different functions that may be used simultaneously or the different functions of the coil may be time-multiplexed. In splitting of the coil into various parts, it is for instance possible to tune out a part of the coil with a parallel circuit tuned to a specific frequency and apply the coil at this frequency as RF communications antenna which is connected to a radio module. The remaining part of the coil may be used for charging a battery or power capacitor via a charging control circuit.

According to yet another embodiment, the screw thread comprises more than one coil, where each of the more than one coil is formed by an electrical wire arranged at least partly within the thread of said screw thread, where the electrical wire of any of the more than one coil follows at least part of the turns of the screw thread. Thus, instead of creating more windings on a single coil, a number of coils in parallel or series can be integrated in the same screw thread whenever it is allowed by the mechanical constraints of the screw thread. The one or more coils are individually accessible, in that each of the coils may be made of a separate electrical wire having connection points. In the case of a number of coils in series, a return path may be absent.

Such a combination may achieve one or more of the following advantages:

skin effect impedance loss improvement;

higher induced voltages;

separated coils cutting an equal field to generate isolated voltages and functions;

transformer with two or more windings for voltage conversion and impedance matching/transformation.

In a further embodiment of the component, one or more electrical contacts on the surface of the screw thread is/are in electrical communication with electrical wire within the thread. Examples of such electrical communication may be electrical contact, electrical connection, and galvanic connection. Thus, the electrical wire embedded within the screw thread may simultaneously be used as a simple electrical connector to matching electrical parts in a matching component arranged for attachment to the component via the screw thread.

For example, if the screw thread of the component is an external thread arranged for matching an internal thread of a second component, the external thread may comprise a number of electrical contacts, each connected to the electrical wire forming the coil, via integrated wires in the external thread. The internal thread of the second component may have an identical number of electrical contacts whose positions exactly match with the contacts on the external thread of the component when being attached to, viz. being screwed into the internal thread of the second component. When the contacts are made sufficiently long and the threads form a robust mechanical construction, reliable electrical connections are obtained.

The component may advantageously be part of an implantable medical device, such as a pace maker, a brain stimulation device, a sensor, etc. The space saving arrangement of the coil within the screw thread of a component is particularly important in implantable medical devices, in particular in deep brain stimulation devices, where there are severe restrictions on the maximum size of implantable devices.

The component may advantageously be a self-tapping screw. This means that the component is able to advance when turned, while creating its own thread in the material into which it is screwed.

According to a second aspect, the invention relates to a modular system comprising:

a first component having an external screw thread, wherein a first electrical wire is arranged at least partly within the thread of said external screw thread and wherein said first electrical wire follows at least part of the turns of the external screw thread; a second component having a internal screw thread; wherein said external screw thread of said first component is arranged to match with said internal screw thread of said second component so as to enable mounting of said first and second component together.

Advantageously, a second electrical wire is arranged in the second component of the modular system, at least partly within the thread of said internal screw thread and wherein said second electrical wire follows at least part of the turns of the internal screw thread.

According to another embodiment of the modular system, one or more first electrical contacts on the surface of the male screw thread is/are in electrical communication with the electrical wire of the first component within the thread; and wherein the internal screw thread of the second component comprises one or more second electrical contacts arranged so as to be in contact with the one or more first electrical contacts of the first component, when the first component and the second component are mounted together.

The different aspects of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

Identical reference numerals denote similar elements throughout the figures.

DETAILED DESCRIPTION OF AN EMBODIMENT

Figure 1:
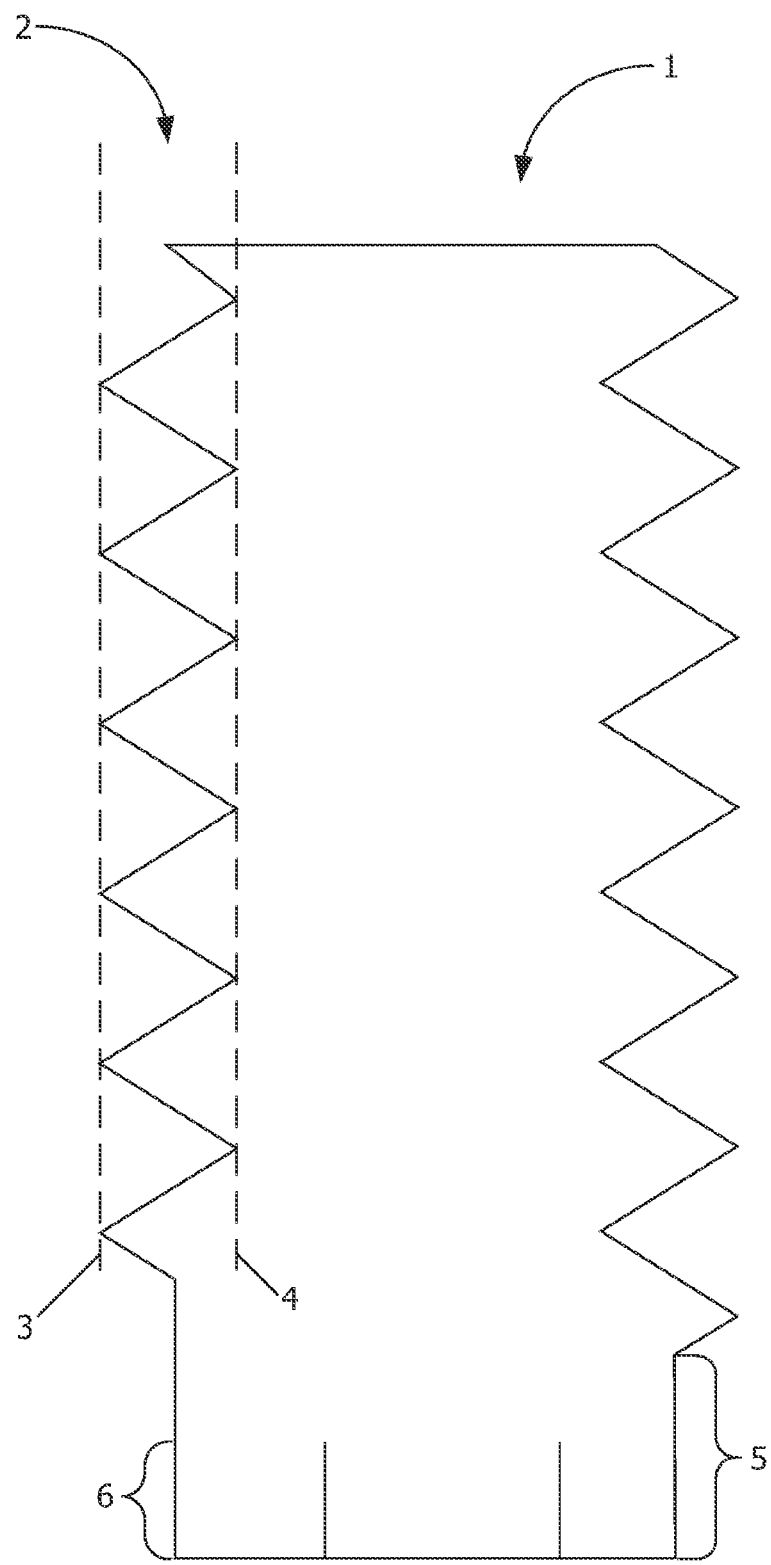
FIG. 1 is a cross section of a component having an external screw thread.

FIG. 1 is a cross section of a component 1 having an external screw thread. The broken lines 3 and 4 delimit the thread 2 of component 1. The term "screw thread" is meant to denote the structure which follows a part of the surface of component 1 and being arranged for fastening to another component. Typically, a screw thread constitutes a helical structure. A screw thread may be a tapered structure; however, it is also conceivable that the screw thread has a cylindrical outline. The term "thread" is meant to denote the part of the circumference of component 1 lying between the broken lines 3 and 4. Thus, in cases where the screw thread of a component has been formed or cut, the term "thread" denotes a part of the component exterior to the bulk of the component, where a part of the material of the component has been removed by e.g. cutting, extrusion, rolling, squeezing, forming or grinding. The term "bulk" of the component is meant to denote the part lying between a central longitudinal axis (not shown) and the line 4, where the line 4 delimits the bulk from the thread. The component 1 comprises an end part 5 having an engagement part 6 for engagement with a tool suitable for holding and/or rotating component 1. The shape of the engagement part 6 may e.g. be hexagonal (see also FIG. 6).

Figure 2A:
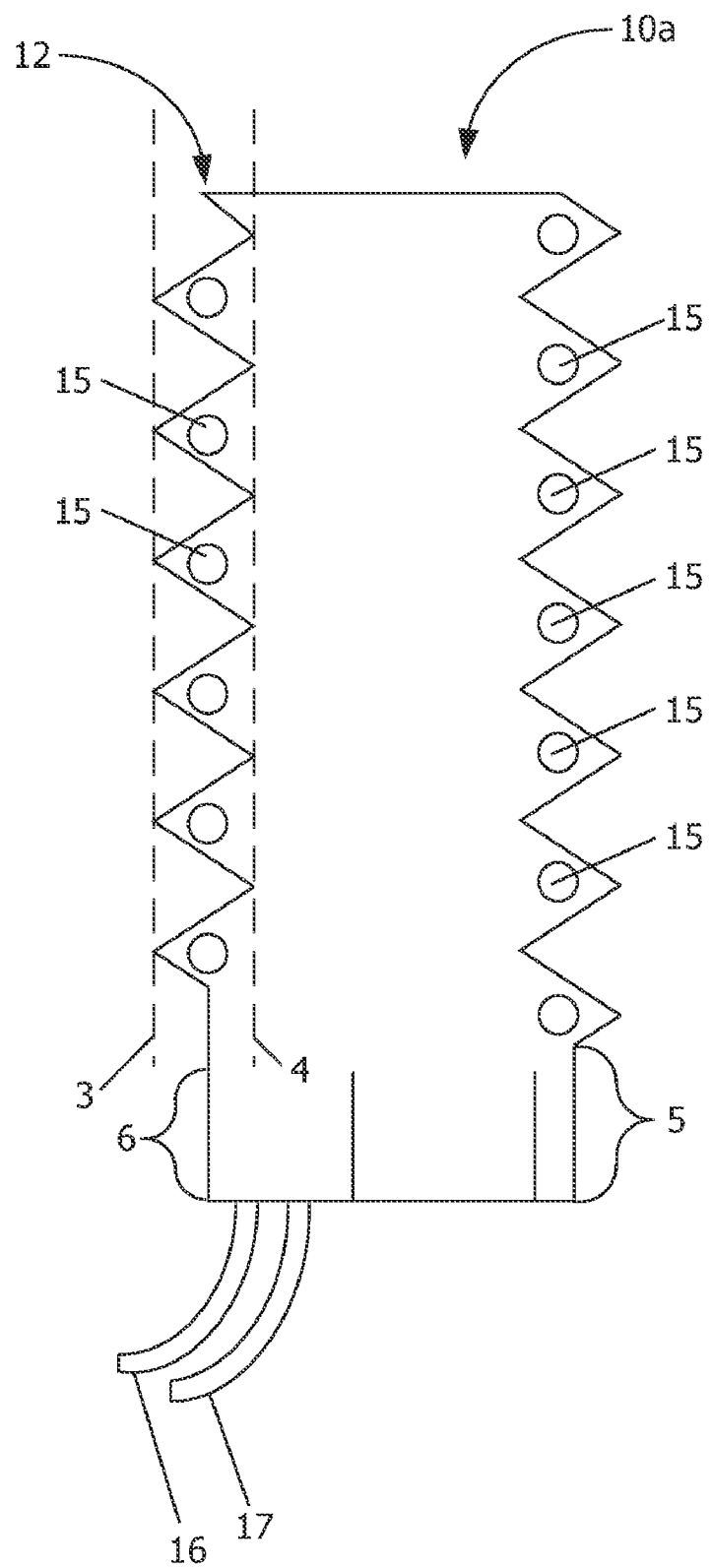
FIGS. 2a, 2b and 2c are cross sections of components according to the invention.

FIG. 2a is a cross section of a component 10a according to the invention. The component 10a has an external screw thread, also denoted a male screw thread. Alternatively, the component according to the invention could have an internal screw thread, also denoted a female screw thread. The lines 3 and 4 delimit the thread 12 of component 10a. Embedded within the thread 12 of the component 10a is an electrical wire 15. The turns of electrical wire 15 follow the helical structure of the screw thread, so that the electrical wire 15 forms a coil. The turns of electrical wire 15 are embedded or integrated within the thread 12, in that the electrical wire 15 lies within the part of the component between the lines 3, 4 delimiting the thread 12. The component 10a comprises an end part 5 having a engagement part 6 for engagement with a tool suitable for holding and/or rotating the component 1. The shape of the engagement part 6 may e.g. be hexagonal (see also FIG. 6). The electrical wire comprises two connection parts 16, 17, extending from the end part 5 of the component 10a. Alternatively, the electrical wire may have connections on the upper end of component 10a according to the orientation of this component in FIG. 2a or the component 10a may have internal electronics and somewhere along the winding, viz. at some of the turns of electrical wire along the line 4, connections may be made to the internal electronics.

Figure 2B:
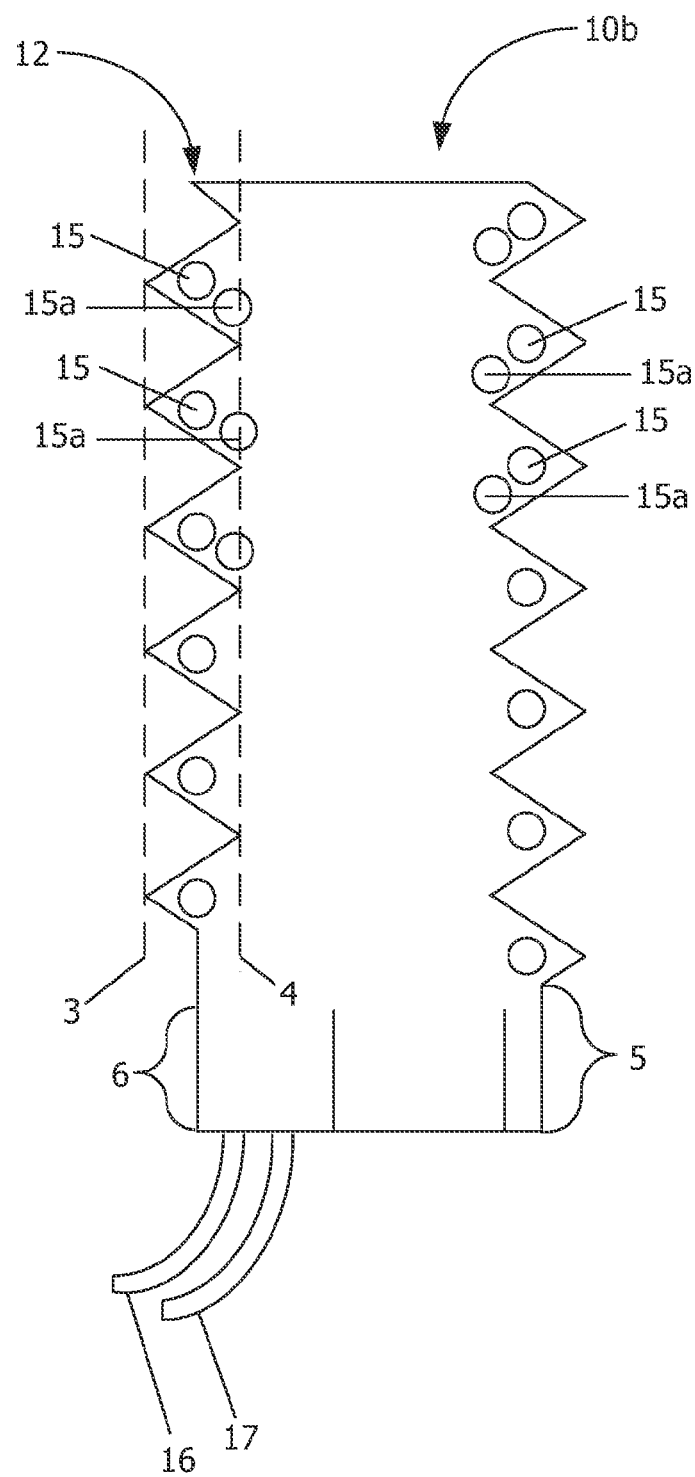

FIG. 2b is a cross section of another component 10b according to the invention. The component 10b has an external screw thread. Alternatively, the component according to the invention could have an internal screw thread. The lines 3 and 4 delimit the thread 12 of the component 10b. Embedded within the thread 12 of the component 10b is an electrical wire 15. The electrical wire 15 follows the helical structure of the screw thread, whereby the electrical wire 15 forms a helical coil.

From FIG. 2b it can be seen that some of the turns of the screw thread comprises two pieces of electrical wire 15, 15a, constituting turns of two different coils or two windings of the same coil. The electrical wire may comprise a return part, e.g. a wire return path, (not shown) bringing the wire along the longitudinal direction of the component 10b in order to let the electrical wire follow some of the turns of the screw thread more than once; in this case the two pieces of electrical wire 15, 15a constitute two windings of the same coil. The magnetic field of the return part is orthogonal to the magnetic field from the coils of the electrical wire 15, 15a within the screw thread, and therefore, ideally, they do no influence each other. The number of times the same screw thread may be wound is limited by the applied wire thickness and the mechanical specifications of the screw thread.

The two electrical wires 15, 15a could alternatively constitute two different or parallel coils of electrical wire.

The turns of electrical wire 15 are totally embedded or integrated within the thread 12, in that the turns of electrical wire 15 lie within the part of the component between the lines 3, 4 delimiting the thread 12. The turns of electrical wire 15a are only partly embedded within the thread 12 of the component 10b, in that they extend into the bulk of the component 10b. Alternatively, the electrical wire and/or the screw thread of the component could be dimensioned so that two or more turns of electrical wire would fit within the turns of the thread of the component 10a.

The wire comprises two connection parts 16, 17 extending from the end part 5 of the component 10b. In the case where the component comprises two parallel coils, two more connections parts (not shown) would extend from the end part 5 of the component. Again, the electrical wire may have connections on the upper end of component 10b as seen in FIG. 2b, or component 10b may have internal electronics and connections may be made to the internal electronics somewhere along the winding, viz. along line 4.

Figure 2C:
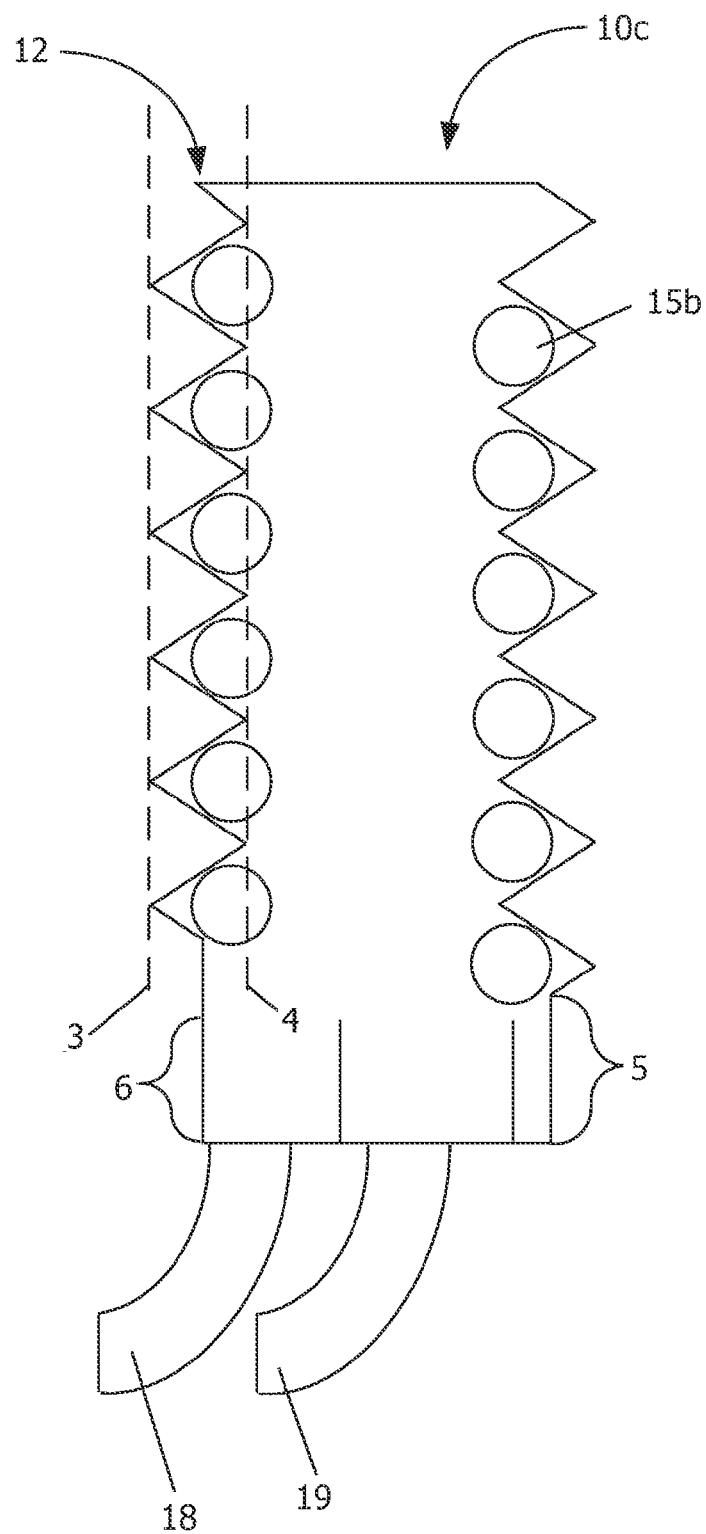

FIG. 2c is a cross section of yet another component 10c according to the invention. The component 10c of FIG. 2c has an external screw thread. Alternatively, the component according to the invention could have an internal screw thread. The lines 3 and 4 delimit the thread 12 of the component 10b. Partly comprised within the thread 12 of the component 10c are turns of electrical wire 15b. The electrical wire 15b follows the helical structure of the screw thread, whereby the electrical wire forms a helical coil.

From FIG. 2c it can be seen that the turns 15b of electrical wire are only partly embedded within or integrated in turns of the thread 12 of the component 10c, in that they extend into the bulk of the component 10c. Even though the turns 15b of electrical wire takes up some of the bulk of the component 10c, the arrangement of FIG. 2c is saving space compared to an arrangement where the turns of a coil of electrical wire would lie totally within the bulk of the component.

The wire comprises two connection parts 18, 19 extending from the end part 5 of the component 10c. Again, the electrical wire may have connections on the upper end of component 10c as seen in FIG. 2c, or component 10c may have internal electronics and connections may be made to the internal electronics somewhere along the winding, viz. along the line 4.

Figure 3:
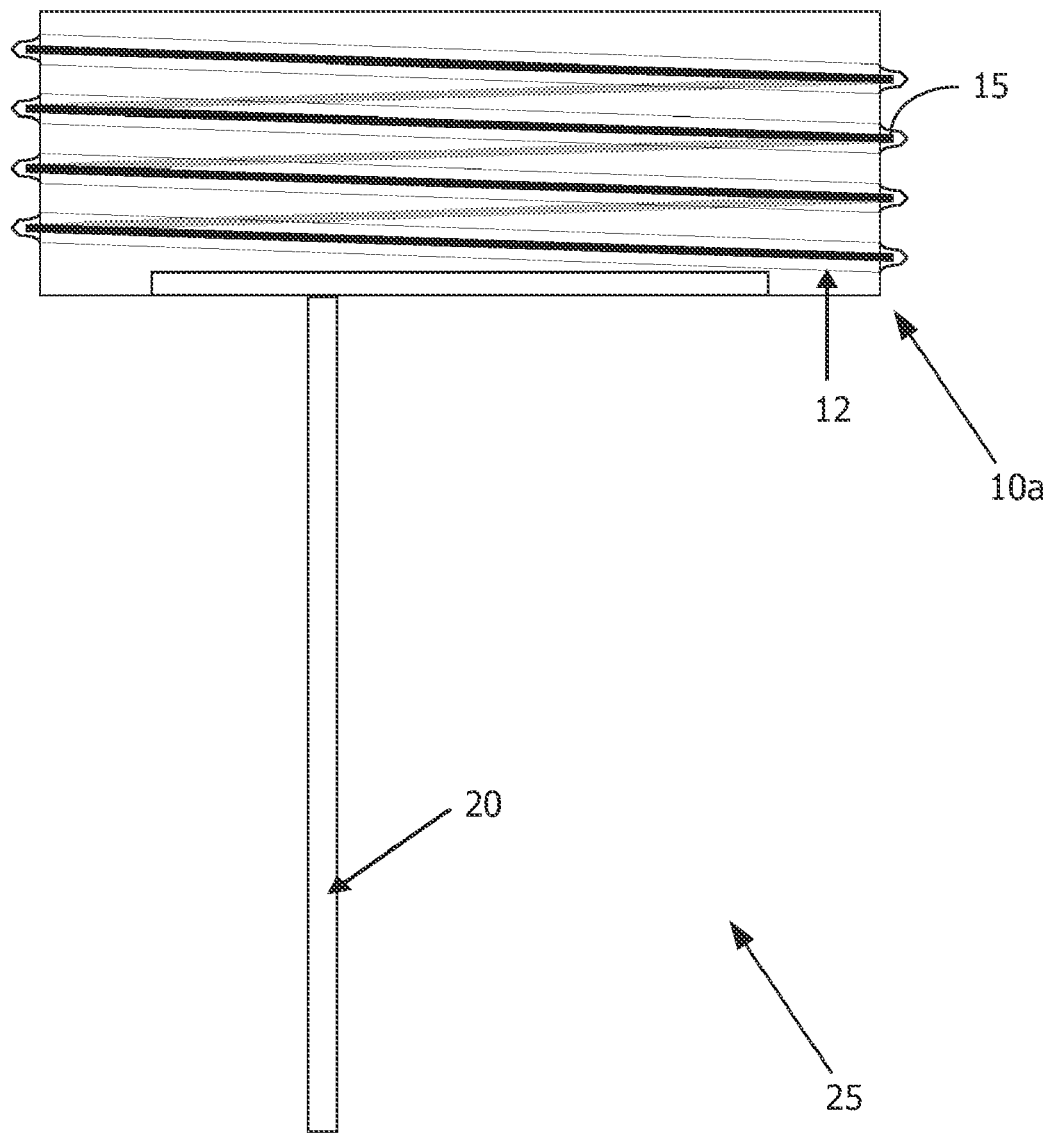
FIG. 3 is a structural diagram of a brain stimulation device comprising a component according to the invention.

FIG. 3 is a structural diagram of a brain stimulation device 25 comprising a component 10a according to the invention. The brain stimulation device moreover comprises a probe 20 extending from and connected to the component 10a. The component 10a comprises an external thread 12 containing an electrical wire 15. The component 10a may contain electronics, for example a pulse generator for brain stimulation via the electrodes at the distal end of the probe. The screw thread 12 of the component 10a may be used for fixating the brain stimulation device 25 into a second component comprising an internal thread matching the thread 12, the second component being arranged to be implanted in the skull of a person. Typically, the second component is firstly implanted in the skull, thereafter the probe 20 is inserted and subsequently the component 10a is connected to the second component by means of the threads. It should be noted, that the component 10a of the brain stimulation device 25 may be inserted directly into the skull of a patient, i.e. the second component described above may be absent. In this case, the component 10a may advantageously be a self-tapping screw so that it may be screwed directly into the skull of a patient. In FIG. 3, the probe is eccentric; however, the component could also be arranged for central mounting of the probe.

Figure 4:
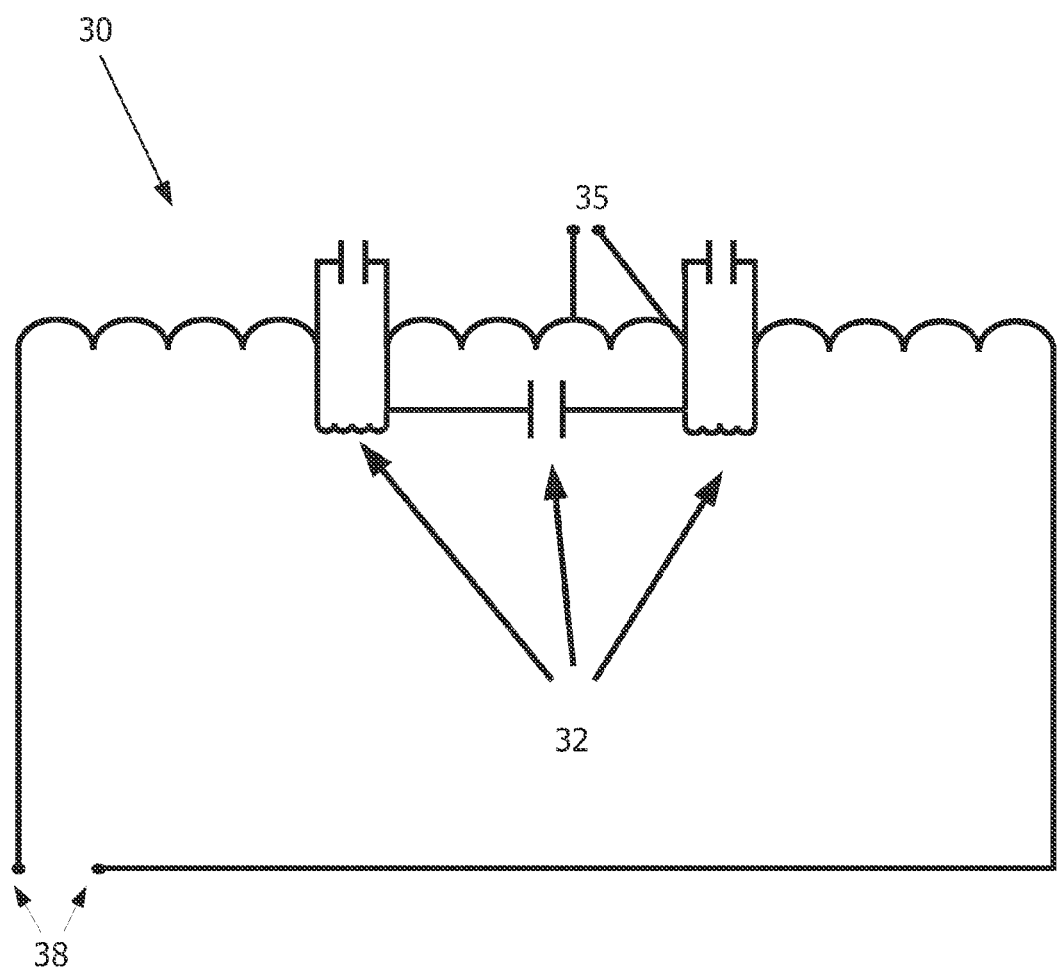
FIGS. 4 and 5 show circuits arranged for splitting the functions of a coil in a component according to embodiments of the invention.

FIG. 4 shows an electrical circuit 30 arranged for splitting the functions of a coil in a component having a screw thread according to an embodiment of the invention. The coil with the electrical circuit 30 may be used for charging a battery or power capacitor via a charging control circuit. An external time-varying electromagnetic field may be applied to transfer energy to the coil; the RF frequency of the external electromagnetic field for charging is typically in the range between 0 and 15 MHz, with typical values of 4 MHZ and 13.56 MHz. The same coil may be applied as RF antenna, where the applied frequency range may be between 400 MHz and 1 GHz, typically 403 MHz.

The circuit 30 comprises two charging coil connections 38, viz. the ends of the electrical wire forming the coil within the component. The coil is split up into three different circuits 32. The middle LC circuit is e.g. tuned to 403 MHz for use as RF antenna, having the radio module connections 35. The other parts of the coil may be tuned to 403 MHz and are used for isolating the antenna part. The complete series connection of coils can be used as charging coil, for example at a frequency of 13.56 MHz.

Figure 5:
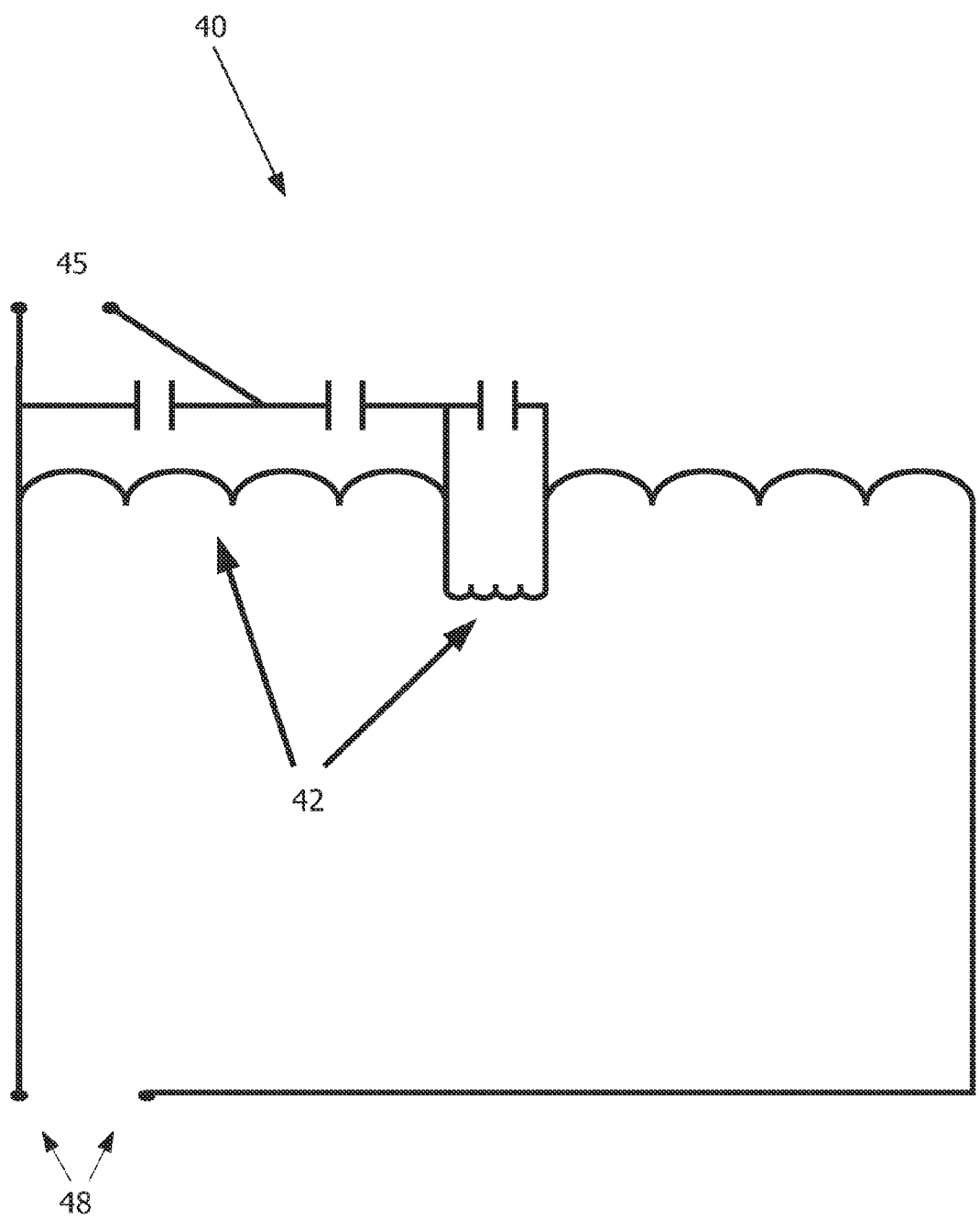

FIG. 5 shows an alternative electrical circuit 40 arranged for splitting the functions of a coil in a component according to the invention. The coil with the electrical circuit 40 may be used for charging a battery or power capacitor via a charging control circuit. Again, an external time-varying electromagnetic field may be applied to transfer energy. This energy can be picked-up by the coil and via a charging control circuit conveyed to a rechargeable battery; the RF frequency of the external electromagnetic field for charging is typically in the range between 0 and 15 MHz, with typical values of 4 MHz and 13.56 MHz. The same coil may be applied as RF antenna, where the applied frequency range may be between 400 MHz and 1 GHz, typically 403 MHz.

The circuit 40 comprises two charging coil connections 48, viz. the ends of the electrical wire forming the coil within the component. The coil is split up into two different circuits 42, e.g. tuned to 403 MHz. One of the circuits 42 may be used as RF antenna, having the radio module connections 45. The complete series connection of coils can be used as charging coil, for example at a frequency of 13.56 MHz.

Other electrical circuits which enable high- and low-frequency RF combinations in a single coil are conceivable. For example, the principle can be applied to tune-out the coil at the MRI RF fields, i.e. 64 MHz in most MRI scanners today, to at least partially protect the sensitive electronics to which the coil is connected.

Figure 6:
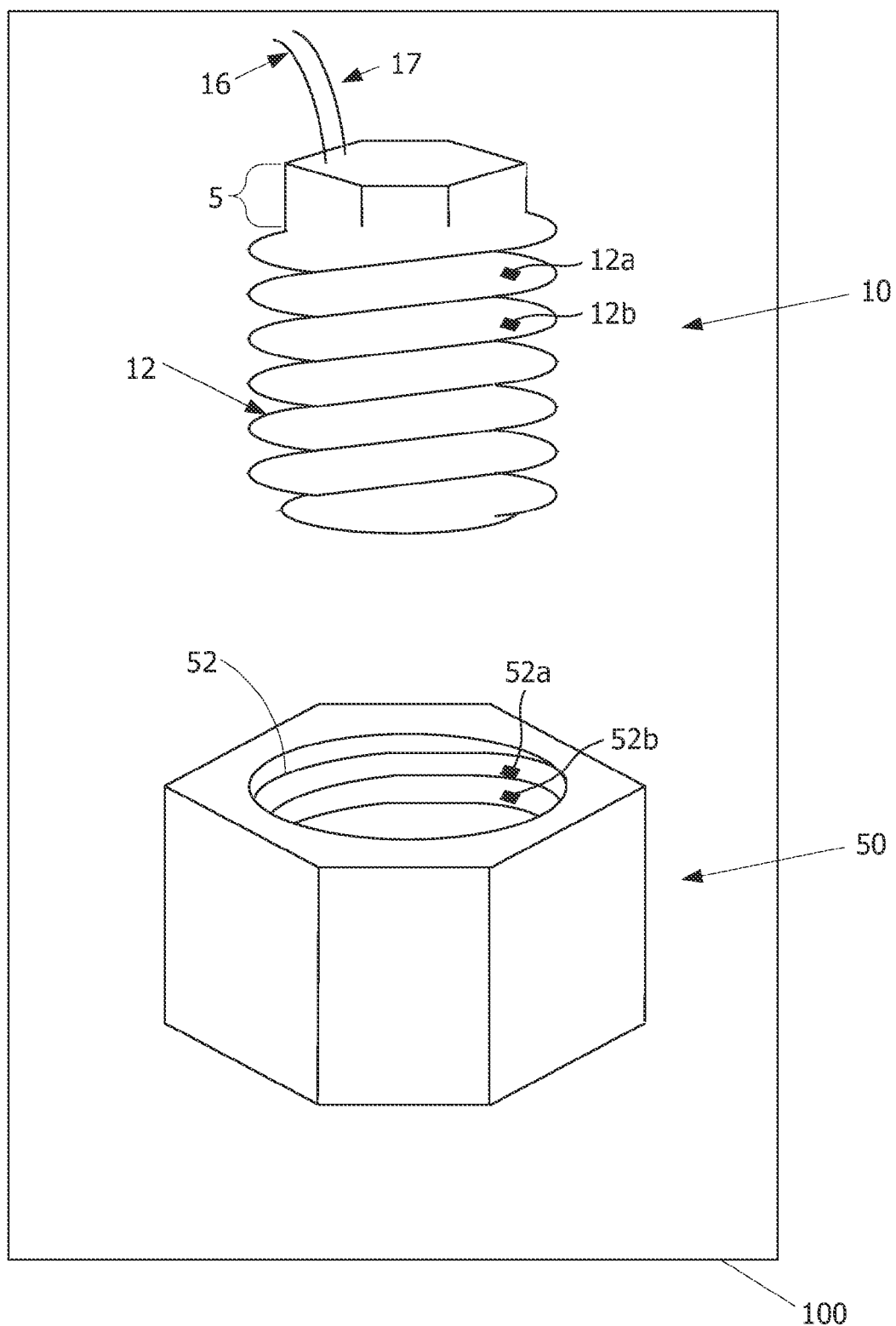
FIG. 6 shows a module according to the invention.

FIG. 6 shows a modular system 100 according to the invention. The modular system 100 comprises a first component 10 having an external screw thread 12. A first electrical wire is arranged at least partly within the thread of said external screw thread and follows at least part of the turns of the external screw thread and forms a first coil. Thus, the first component 10 could be a component as described in relation to any of the FIGS. 2a to 2c. The electrical wire within the thread of the first component 10 comprises two connection parts 16, 17 extending from the end part 5 of the component 10.

The modular system 100 moreover comprises a second component 50 having an internal screw thread 52, where the external screw thread 12 of the first component 10 is arranged to match with the internal screw 52 thread of the second component 50 so as to enable mounting of said first and second components together.

In one embodiment of the modular system 100, a second electrical wire (not shown) is arranged at least partly within the thread of the internal screw thread 52 of the second component 50, where the second electrical wire follows at least part of the turns of the internal screw thread. Thus, the second electrical wire may form at least part of a second coil. When the first and second components 10, 50 are mounted together, the first coil will be at least partly arranged so as to surround the second coil in the screw thread 52. Thereby, the first and second component 10, 50 of the modular system 100 may communicate with each other without direct electrical contact. Such communication includes wireless transport of energy because such two coils form a transformer.

In another embodiment, one or more first electrical contacts 12a and 12b on the surface of the external screw thread is/are in electrical communication with the electrical wire of the first component within the thread 12, and the internal screw thread 52 of the component 50 comprises corresponding one or more second electrical contacts 52a and 52b arranged so as to be in contact with the one or more first electrical contacts of the first component 10, when the first component 10 and the second component 50 are mounted together. Again, examples of electrical communication may be electrical contact, electrical connection, and galvanic connection.

The electrical contacts of the first and/or third component may be connected by a single wire to electrical circuitry; alternatively the contacts may be connected by separate wires so that each contact may be used individually.

The two above embodiments of the modular system 100 may be combined so that the component 50 comprises both a coil within the thread 52 and contacts on the surface of the thread 52 connected to the coil within the thread 52 or to other electrical wires within the component 50.

In summary, components having a screw thread useful for mechanical fixation of the component to a corresponding component, may be equipped with electrical wire following at least part of the turns of the screw thread and thereby forming at least a part of a coil. The corresponding component may have a matching screw thread, or the component of the invention may be self-tapping, in which case a matching screw thread in the corresponding component would be superfluous. The coil may be used as charging and/or power-conversion coil and/or communication antenna. The reuse of the screw thread for a coil maximizes the coil area without consuming extra space of the component. This is in particular useful in medical electrical implant devices, such as a pace maker or a neuron pace maker in deep brain stimulation, in that the maximum size of such a pace maker is very limited.

Moreover, the screw thread of such components may additionally comprise connectors for providing electrical connection to other electrical parts in a matching component.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A component comprising:
   a screw thread having a helical structure for fastening, wherein an electrical wire is embedded at least partly within a thread of the screw thread, wherein the electrical wire follows at least part of a plurality of turns of the screw thread.

2. The component according to claim 1, wherein at least part of the turns of the screw thread comprise more than one coil winding of electrical wire.

3. The component according to claim 2, wherein the electrical wire comprises a return part.

4. The component according to claim 1, wherein the electrical wire constitutes a coil arranged to perform more than one electromagnetic function, separated by frequency filters.

5. The component according to claim 1, wherein another electrical wire is embedded at least partly within the thread of the screw thread, following at least part of the turns of the screw thread, each of the electrical wires forming corresponding coils.

6. The component according to claim 1, further comprising:
   one or more electrical contacts on a surface of the screw thread and in electrical communication with the electrical wire embedded within the thread.

7. An implantable medical device comprising the component according to claim 1.

8. The component according to claim 1, wherein the component is a self-tapping screw.

9. A modular system comprising:
   a first component having an external screw thread, wherein a first electrical wire is embedded in the first component, at least partly within a thread of the external screw thread, and wherein the first electrical wire follows at least part of a plurality of turns of the external screw thread; and
   a second component having an internal screw thread, wherein the external screw thread of the first component is arranged to match with the internal screw thread of the second component to enable mounting of the first and second components together.

10. The modular system according to claim 9, wherein a second electrical wire is embedded in the second component, at least partly within a thread of the internal screw thread, and wherein the second electrical wire follows at least part of a plurality of turns of the internal screw thread.

11. The modular system according to claim 9, wherein the first component comprises one or more first electrical contacts on a surface of the external screw thread in electrical communication with the electrical wire of the first component embedded within the thread, and
    wherein of the second component comprises one or more second electrical contacts arranged to be in contact with the one or more first electrical contacts of the first component, when the first component and the second component are mounted together.

12. A fastening component comprising:
a bulk portion;
a thread portion having a helical structure, comprising a plurality of turns, formed around the bulk portion and configured for fastening; and
an electrical wire embedded within at least one of the bulk portion and the thread portion, the electrical wire following at least part of the plurality of turns.

* * * * *